United States Patent
Armstrong et al.

(10) Patent No.: US 6,695,820 B1
(45) Date of Patent: Feb. 24, 2004

(54) BLEED BACK CONTROL ASSEMBLY

(75) Inventors: Kenneth K. Armstrong, Riverside, CA (US); Vito Foggetti, Temecula, CA (US); Charles R. Peterson, Murrieta, CA (US); Albert A. Quinones, Murrieta, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 69 days.

(21) Appl. No.: 09/990,853

(22) Filed: Nov. 16, 2001

Related U.S. Application Data

(63) Continuation-in-part of application No. 09/267,754, filed on Mar. 11, 1999, now Pat. No. 6,331,176.

(51) Int. Cl.⁷ .................................... A61M 25/00
(52) U.S. Cl. .................................... 604/256
(58) Field of Search ............... 604/167.01–167.05, 604/246, 256, 164.01–164.04, 533–539

(56) References Cited

U.S. PATENT DOCUMENTS

| | | |
|---|---|---|
| 4,341,239 A | 7/1982 | Atkinson |
| 4,421,296 A | 12/1983 | Stephens |
| 4,581,020 A | 4/1986 | Mittleman |
| 4,610,469 A | 9/1986 | Wolff-Mooij |
| 4,634,432 A | 1/1987 | Kocak |
| 4,638,668 A | 1/1987 | Leverberg et al. |
| 4,874,378 A | 10/1989 | Hillstead |
| 4,886,507 A | 12/1989 | Patton et al. |
| 4,935,010 A | 6/1990 | Cox et al. |
| 4,960,412 A | 10/1990 | Fink |
| 5,057,084 A | 10/1991 | Ensminger et al. |
| 5,059,186 A | 10/1991 | Yamamoto et al. |
| 5,064,416 A | 11/1991 | Newgard et al. |
| 5,085,645 A | 2/1992 | Purdy et al. |
| 5,092,840 A | 3/1992 | Healy |
| 5,106,054 A | 4/1992 | Mollenauer et al. |
| 5,125,915 A | 6/1992 | Berry et al. |
| 5,147,336 A | 9/1992 | Wendell et al. |
| 5,195,980 A | 3/1993 | Catlin |
| 5,269,764 A | 12/1993 | Vetter et al. |
| 5,306,243 A | 4/1994 | Bonaldo |
| 5,324,271 A | 6/1994 | Abiuso et al. |
| 5,338,314 A | 8/1994 | Ryan |
| 5,376,077 A | 12/1994 | Gomringer |
| 5,382,230 A | 1/1995 | Bonn |

(List continued on next page.)

FOREIGN PATENT DOCUMENTS

| | | |
|---|---|---|
| EP | 0 658 357 A2 | 6/1995 |
| EP | 0 875 262 A2 | 11/1998 |

OTHER PUBLICATIONS

Nycomed Amersham Medica Systems, "Easi–Ketch: A Revolutionary Y–Adaptor for an Easier, Cleaner, Safer Procedure", Apr. 1998 Rev. A, brochure, 8 pages.

Primary Examiner—Brian L. Casler
Assistant Examiner—Kevin C. Sirmons
(74) Attorney, Agent, or Firm—Fulwider Patton Lee & Utecht, LLP

(57) ABSTRACT

A bleed back control assembly for controlling blood loss during catheterization procedures includes a side arm body having a proximal end engaging and retaining a cap assembly and a seal assembly. The seal assembly includes a single elastomeric bleed back seal. The bleed back seal has an aperture and is normally closed. The bleed back seal self-sizes to devices introduced through the aperture. The cap assembly includes a funnel cap having a dilator. Depressing the funnel cap causes the dilator to open the aperture in the bleed back seal. A spring, wound around the dilator, biases the funnel cap to its original position. The side arm body includes a secondary branch having a lumen, and a finger rest on the exterior of the secondary branch.

27 Claims, 8 Drawing Sheets

U.S. PATENT DOCUMENTS

| | | |
|---|---|---|
| 5,458,640 A | 10/1995 | Gerrone |
| 5,474,536 A | 12/1995 | Bonaldo |
| 5,478,331 A | 12/1995 | Heflin et al. |
| 5,591,137 A | 1/1997 | Stevens |
| 5,599,305 A | 2/1997 | Hermann et al. |
| 5,599,327 A | 2/1997 | Sugahara et al. |
| 5,820,600 A | 10/1998 | Carlson et al. |
| 5,911,710 A * | 6/1999 | Barry et al. ............... 604/249 |
| 5,935,112 A * | 8/1999 | Stevens et al. ............ 604/256 |
| 6,287,280 B1 | 9/2001 | Lampropoulos |

* cited by examiner

BLEED BACK CONTROL ASSEMBLY

This application is a continuation-in-part of U.S. patent application Ser. No. 09/267,754, filed Mar. 11, 1999, U.S. Pat. No. 6,331,176 which is hereby incorporated by reference in its entirety.

BACKGROUND OF THE INVENTION

This invention relates generally to a bleed back control assembly for controlling blood loss during vascular diagnostic or interventional procedures, such as insertion and removal of catheters from the blood vessels of a patient.

Treatment of patients with diseases, such as coronary heart disease, may involve the use of catheters, balloon catheters, stents, and other vascular intervention devices which are introduced transluminally, i.e., to and through the interior of a blood vessel. Catheterization procedures often include the use of a hemostatic valve to reduce blood loss.

It is known in the art to provide a large bore rotating hemostasis valve (RHV) which attaches to the end of a guiding catheter and acts as an open/close valve. After a device is introduced into the lumen of an RHV, the RHV serves as a seal around the device to reduce blood loss. An RHV must be opened to allow introduction of an interventional device into the lumen of the RHV, and must be closed to control blood loss while allowing device adjustment, such as moving it back and forth. A doctor must adjust a screw cap of a conventional RHV in order to adjust the seal around various devices introduced axially through the lumen of the RHV. A conventional RHV may utilize a Touhy-Bourst seal design, which may be opened and closed by the user, but such a seal allows fluid to escape until properly adjusted. A significant amount of blood may be lost during these adjustments of the RHV which are required in order to move a device, such as a catheter, in and out of the RHV. When the RHV is not adjusted to seal around the device introduced in the lumen of the RHV, there is no mechanism for inhibiting substantial bleed back or blood loss.

Accordingly, a conventional RHV allows excessive blood loss when the RHV is not adjusted or whenever the RHV is in the open position. The excessive blood loss also creates a more ensanguined operating environment for the user of the RHV, increasing risks associated with unwanted exposure to blood (or other fluids) and making more difficult the manipulation or operation of devices.

SUMMARY OF THE INVENTION

The bleed back control assembly permits diagnostic or interventional vascular procedures, such as insertion of devices like catheters, guide wires, or stent delivery systems into the blood vessels of a patient, while controlling and significantly reducing the amount of blood loss, when the catheter is adjusted or moved. The bleed back control assembly includes an elastomeric bleed back control seal around the intervention device (such as, but not limited to, a catheter). In accordance with these and other aspects of the invention, the bleed back control assembly controls blood loss during insertion, movement, and removal of a vascular intervention device (such as a catheter) from the assembly.

DETAILED DESCRIPTION OF THE EMBODIMENTS

The components of an embodiment of the bleed back control assembly 1 are shown in relation one to the other in FIGS. 1a through 1d.

Figure 1A:
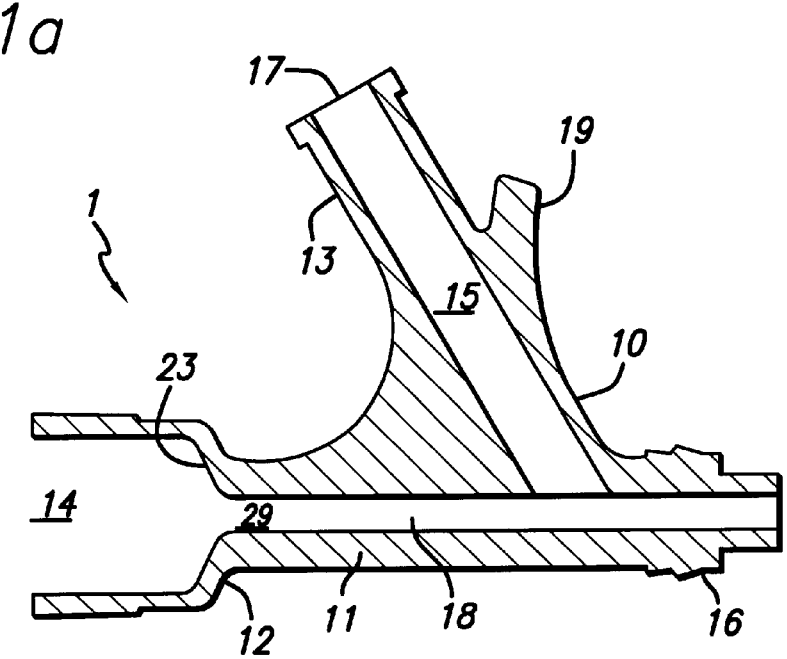
FIG. 1a is a cross-sectional view of a side arm body in accordance with the present invention.

Referring to FIG. 1a, a side arm body 10 has a proximal end 12 with a seal cavity 14 formed therein, the side arm body 10 also has a distal end 16. The side arm body 10 has a primary branch 11 and a secondary branch 13. A primary lumen 18 is formed through the primary branch 11 of the side arm body 10 and connects the proximal end 12 to the distal end 16. The side arm body 10 is thus a tube having a lumen allowing fluid (such as blood) to communicate from one end to the other. Fluid may also communicate between the primary lumen 18 and the seal cavity 14. A secondary lumen 15 is formed through the secondary branch 13 of the side arm body 10. Fluid may also communicate between the lumen 18 of the primary branch 11 and the lumen 15 of the secondary branch 13.

Figure 1B:
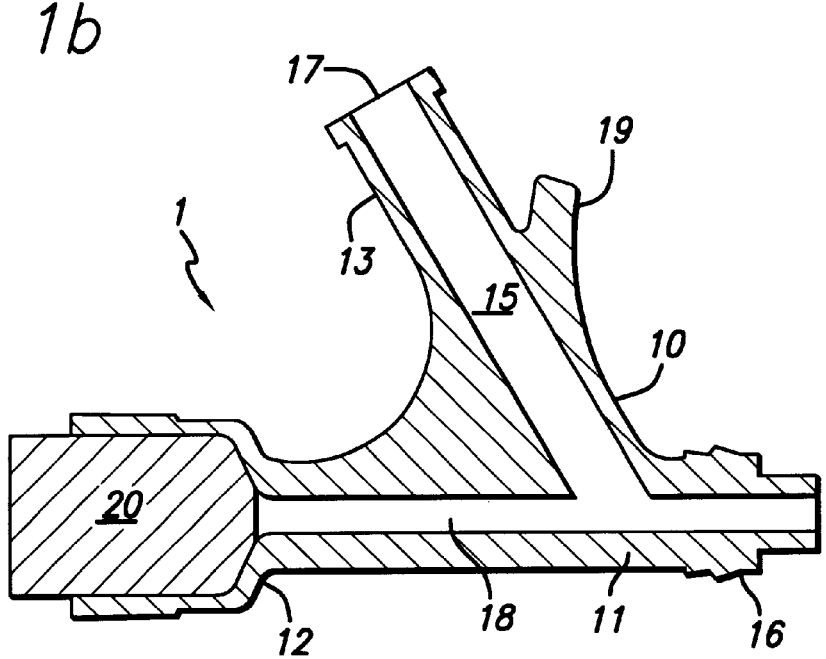
FIG. 1b is a cross-sectional view of a side arm body and seal assembly in accordance with the present invention.

Referring to FIG. 1b, a seal assembly 20 is held within seal cavity 14 at the proximal end 12 of side arm body 10. The seal assembly 20 is generally formed to conform to the shape of the interior surface 23 of the seal cavity 14. As discussed further below, the seal assembly 20 includes a seal made of an elastic and resilient material which may be readily deformed or stretched depending on user operation, and will return to its original shape and position when released or disengaged by the user.

Figure 1C:
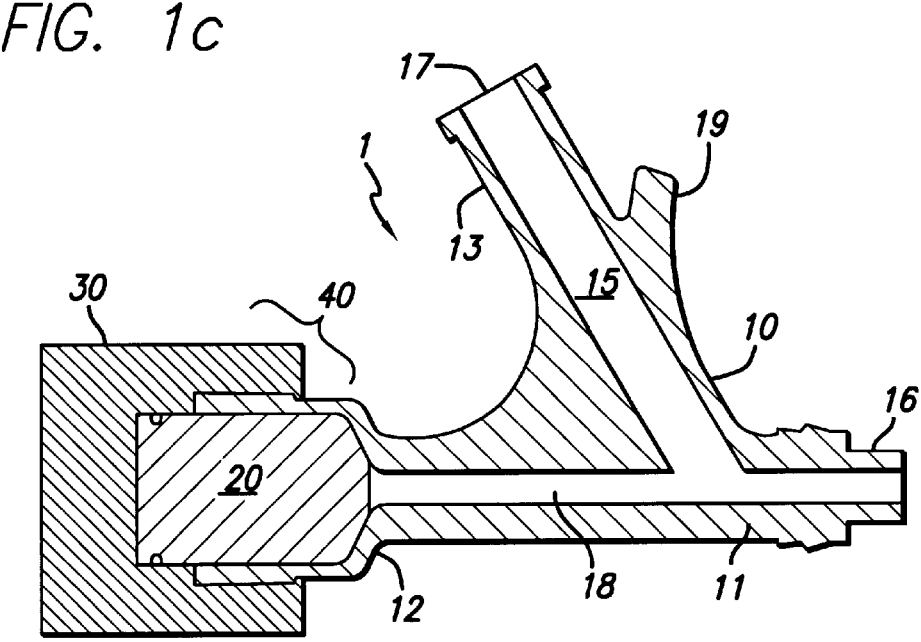
FIG. 1c is a cross-sectional view of a side arm body, a seal assembly, and a cap assembly in accordance with the present invention.

Referring to FIG. 1c, the cap assembly 30 is connected to the seal assembly 20 and is also connected to the exterior surface of the seal cavity 14 at the proximal end 12 of the side arm body 10. The cap assembly 30 contains the seal assembly 20 within the seal cavity 14 and, as described further below, allows user operation and adjustment of the seal assembly 20. As described further below, the user may adjust the seal assembly 20 to either open or close access to the primary lumen 18 of the side arm body 10. The seal body 40 comprises the seal assembly 20 and the cap assembly 30. As shown in FIG. 1c, a bleed back control assembly 1 in accordance with one aspect of the invention comprises the side arm body 10 connected to the seal body 40 at the proximal end 12 of the side arm body 10.

Figure 1D:
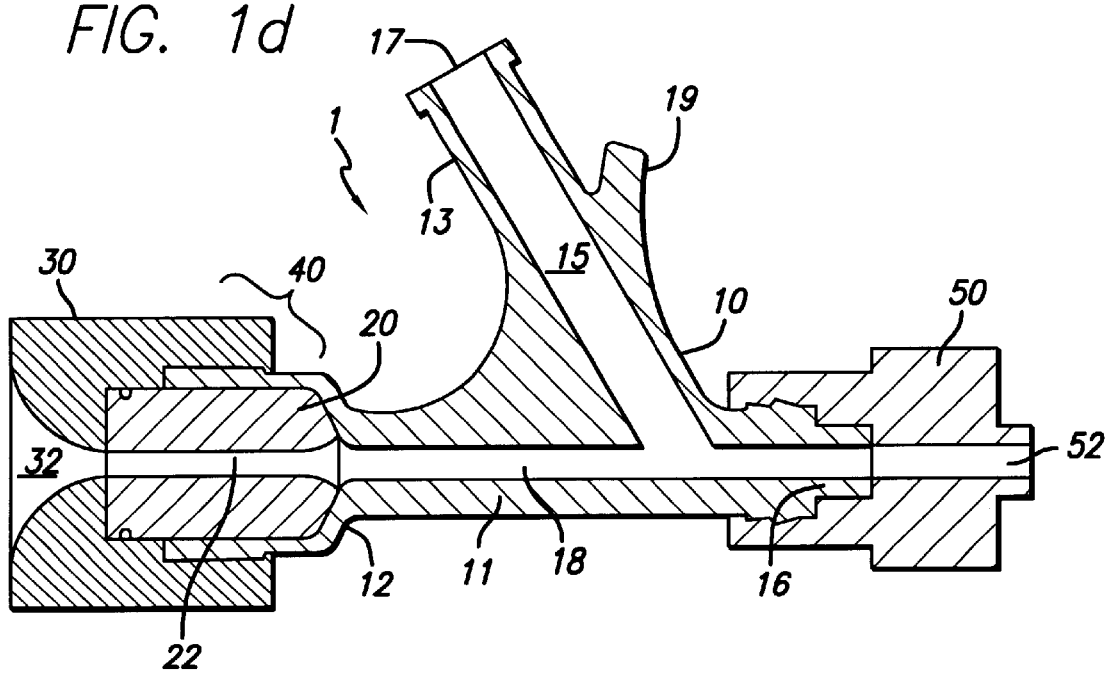
FIG. 1d is a cross-sectional view of a bleed back control assembly in accordance with the present invention.

Referring to FIG. 1d, another embodiment of the bleed back control assembly 1 in accordance with the invention comprises the side arm body 10 having a proximal end 12 and a distal end 16. A seal body 40, comprising seal assembly 20 connected to cap assembly 30, is attached to proximal end 12 of side arm body 10. The seal body 40 includes an elastomeric seal. The cap assembly 30 retains the seal within the seal cavity 14. The seal assembly 20 has an aperture 22 formed therethrough, and the cap assembly 30 has an aperture 32 which is axially aligned with and proximal to the aperture of the seal assembly 20. The aperture 22 of the seal assembly 20 is axially aligned with and proximal to the primary lumen 18.

A male luer connector 50 is connected to the distal end 16 of the side arm body 10. The luer connector 50 has a lumen 52 which connects proximally with the distal end 16 of the primary lumen 18 of the side arm body 10.

The bleed black control assembly 1 may be operated by inserting a vascular intervention device (such as a catheter) through the aperture 32 of the cap assembly 30, then through the aperture 22 of the seal assembly 20, into the lumen 18 of the side arm body 10, through the lumen 52 of the luer connector 50, and ultimately into a patient's body. A user may operate the cap assembly 30 by depressing the cap assembly 30 to open or close the seal assembly 20. The seal assembly 20 provides control over blood loss during insertion and removal of vascular intervention devices through bleed back control assembly 1, as described further below.

Referring to FIGS. 1a to 10c, the structures of side arm body 10 and seal body 40 are shown. Side arm body 10 will be discussed first.

Side Arm Body

Referring to FIGS. 1a to 1d, 2, 4a, and 4b, the side arm body 10 is substantially Y-shaped and consists of a straight primary branch 11 and a secondary branch 13. Lumens 15 and 18 are formed within both the secondary branch 13 and the primary branch 11, respectively.

The lumen 15 of secondary branch 13 provides access to, and is in fluid communication with, the lumen 18 of primary branch 11. The secondary branch 13 can be used for, but is not limited to, contrast injections and drug delivery. For example, the secondary branch 13 may also be used for flushing the system with saline, or any other appropriate uses. The secondary branch 13 of the side arm body 10 is formed, in one embodiment, at approximately a 60 degree angle from primary branch 11. The invention is not limited by the angle at which secondary branch 13 connects with primary branch 11. A port 17 is formed at the end of secondary branch 13, and the port 17 provides connections for injections and other drug or fluid delivery devices.

Referring to FIGS. 1a to 1d, 2, and 4a, a finger rest 19 is formed on the exterior surface of the secondary branch 13. The finger rest 19 is formed, in one embodiment, at approximately 30 degrees from the secondary branch 13. In another embodiment, the angle at which the finger rest 19 is formed may be 20 degrees, 40 degrees, or any other suitable angle. The invention is not limited by the angle at which the finger rest 19 connects with the secondary branch 13. The finger rest 19 is sufficiently large enough to fit at least one finger of an adult user of the bleed back control assembly 1. The finger rest 19 provides the user with improved gripping of the bleed back control assembly 1.

In another embodiment, a finger rest 19 is formed on the exterior surface of the primary branch 11 of the side arm body 10. In this embodiment, the finger rest 19 on the primary branch 11 may be either in place of, or in addition to, a finger rest 19 on the secondary branch 13 of the side arm body 10.

The primary branch 11 of the side arm body 10 has two ends: a proximal end 12 and a distal end 16. A seal cavity 14 is formed within the proximal end 12 of the primary branch 11 of the side arm body 10. The seal cavity 14 is concentric with, and provides access to, the lumen 18 formed axially through the primary branch 11. The seal cavity 14 has a wider diameter than the diameter of the lumen 18. The invention is not limited by the difference between the diameters of the seal cavity 14 and the lumen 18. The lumens 15 and 18 may taper or change diameters along their lengths. The invention is not limited by whether the lumens 15 or 18 taper, or by the amount by which each or either lumen tapers.

Figure 2:
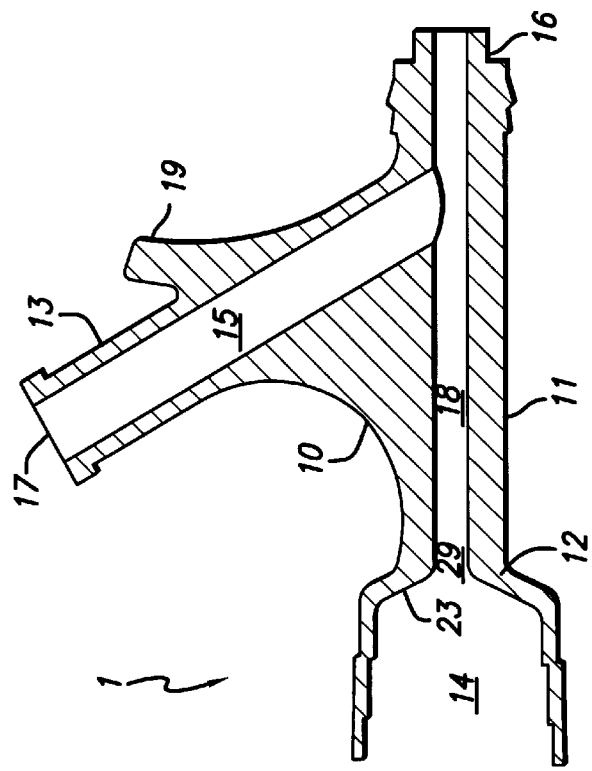
FIG. 2 is an exploded view of a seal body and side arm body of a bleed back control assembly in accordance with the present invention.
Figure 2:
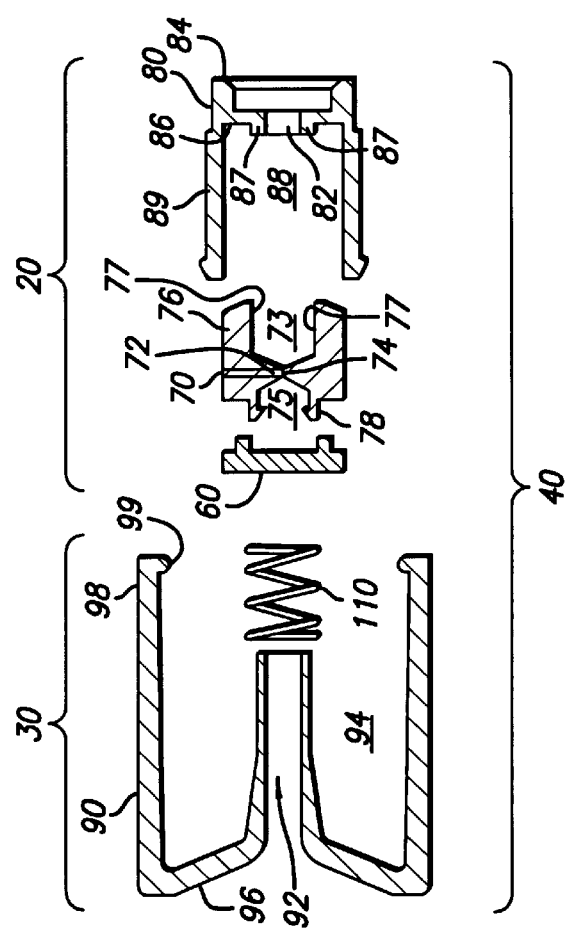

Referring to FIGS. 1a and 2, the seal cavity 14 has an interior surface 23 which is adjacent to aperture 29 connecting the seal cavity 14 to lumen 18. The seal cavity 14 preferably has several staggered inner diameters corresponding to the outer diameters of the seal assembly 20. The exterior surface of the proximal end 12 of the side arm body preferably includes a jutting outer edge 21 for engaging and preventing undesired axial movement of the cap assembly 20.

Figure 4A:
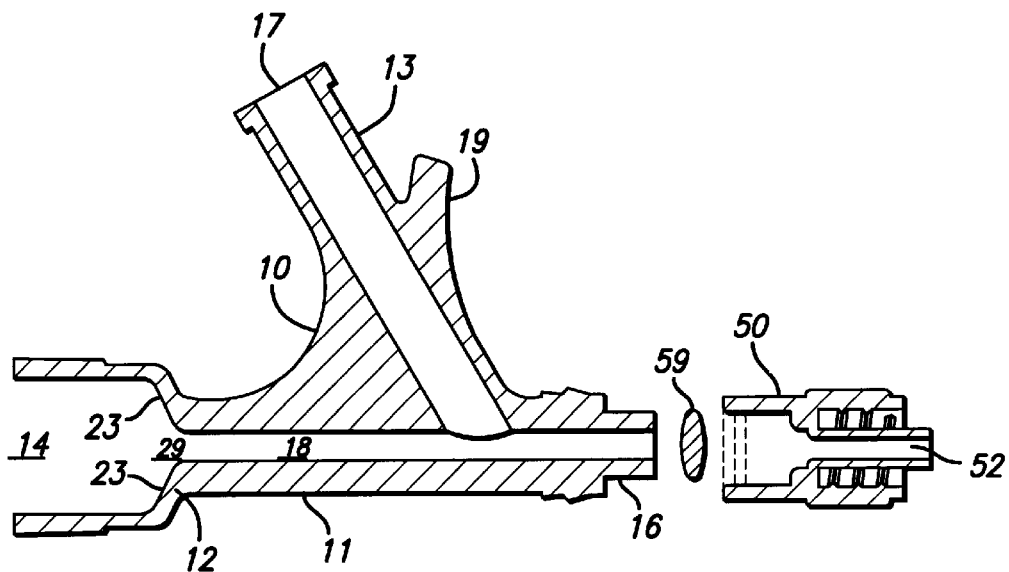
FIG. 4a is an exploded view and FIG. 4b is a cross-sectional view of a side arm body and male luer connector in accordance with the present invention.
Figure 4B:
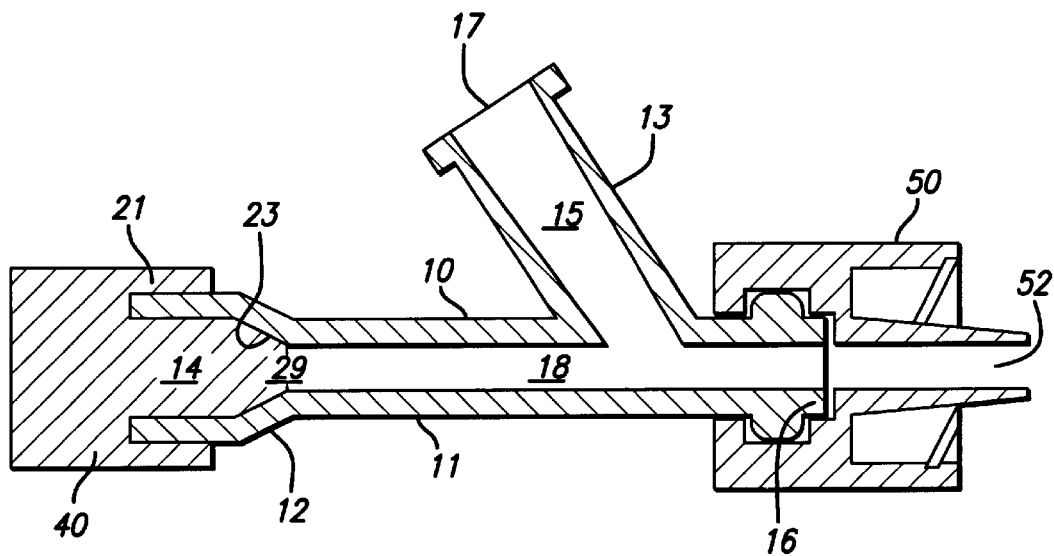

Referring to FIGS. 4a and 4b, distal end 16 of side arm body 10 is connected to a male luer connector 50. Luer connector 50 has a lumen 52 which connects proximally with the distal end of lumen 18. Male luer connector 50 may be 360 degrees rotatable or any other appropriate amount of rotation. While a luer connector 50 is shown connected to the distal end 16 of side arm body 10, the invention is not limited by whether any structures are connected to distal end 16 nor by what those structures are. Those of ordinary skill will appreciate that other appropriate devices may be connected to distal end 16 of side arm body 10 without departing from the scope of the invention. In an alternate embodiment, luer connector 50 is formed integrally as part of distal end 16 of side arm body 10.

The side arm body 10 and luer connector 50 may be formed of any appropriate polymeric material (either thermoplastic or thermosetting). In one embodiment, the side arm body 10 and luer connector 50 are formed of polycarbonate, and may be formed of radiation grade or e-beamable polycarbonate.

In one embodiment, an O-ring 59 is interposed at the connection between distal end 16 of side arm body 10 and luer connector 50. The O-ring 59 may be a conventional O-ring gasket or seal formed of an appropriate elastic material. In one embodiment, O-ring 59 is formed of black color ethylene propylene diene monomer having a hardness of 70±5 Shore-A. An appropriate lubricant may be used with the O-ring 59, such as Dow Corning 360 Medical Fluid, 350 centistoke viscosity (referred to as "Dow 360"). In one embodiment, a mixture of alcohol and Dow 360 may be used as a lubricant for the O-ring 59. Alternatively, O-ring 59 may be lubricated with a coating of a mixture of alcohol and dichloromethane followed by a successive coating of a mixture of alcohol, dichloromethane, and Dow 360. The invention is not limited by the type of O-ring 59 or connector 50 used, nor by the type of lubricant used for the O-ring 59.

Seal Body

As previously discussed, the seal body 40 comprises the seal assembly 20 connected to the cap assembly 30. The cap assembly 30 is connected to the exterior surface of the seal cavity 14. The cap assembly 30 is connected to the proximal end of side arm body 10, and the cap assembly 30 holds the seal assembly 20 within the seal cavity 14.

Figure 3:
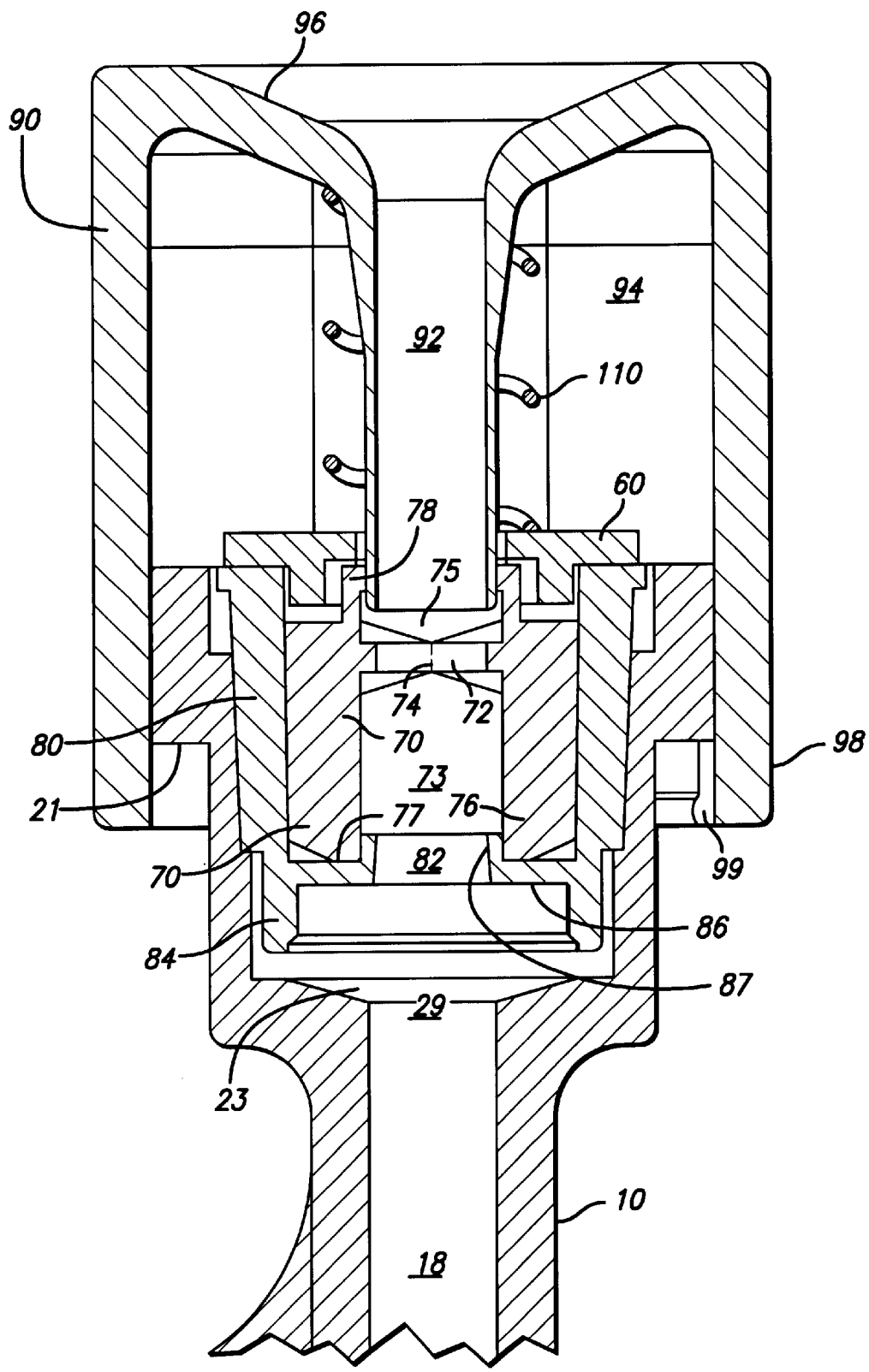
FIG. 3 is a cross-sectional view of a seal body and a proximal end of a side arm body of a bleed back control assembly in accordance with the present invention.

Referring to FIG. 2, the seal assembly 20 comprises the bleed back control seal 70, the seal holder 80, and the seal retainer 60. The cap assembly 30 comprises the funnel cap 90 and return spring 110. FIG. 2 shows these components in exploded view, and FIG. 3 shows these components assembled in relation to each other, as well as in relation to the proximal end 12 of the side arm body 10. In the orientation of FIG. 3, the proximal end of the seal body 40 is shown at the top of the figure. Each component will be discussed in turn.

Seal Assembly

Figure 6A:
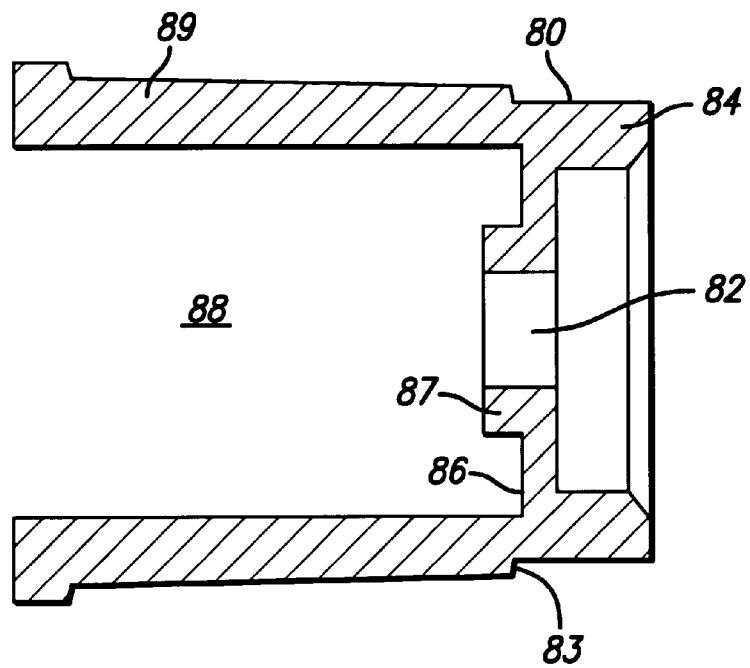
FIG. 6a is a cross-sectional view and FIG. 6b is a perspective view of a seal holder in accordance with the present invention.
Figure 6B:
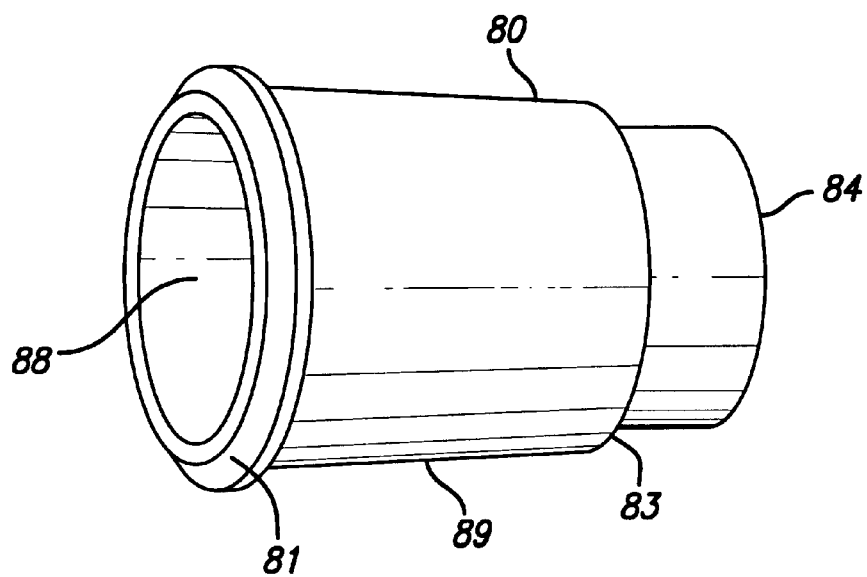
Figure 7:
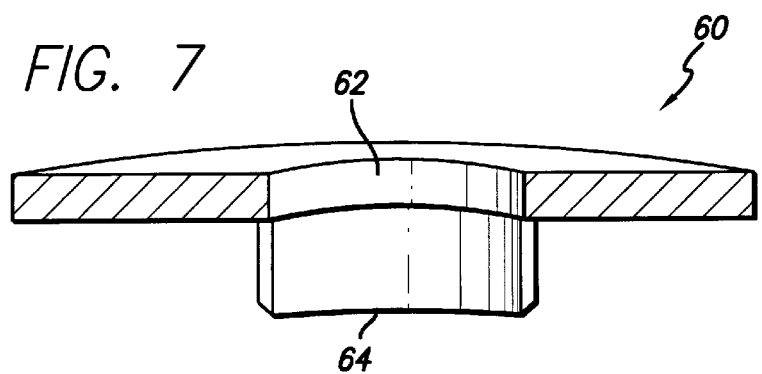
FIG. 7 is a cross-sectional view of a seal retainer in accordance with the present invention.
Figure 8A:
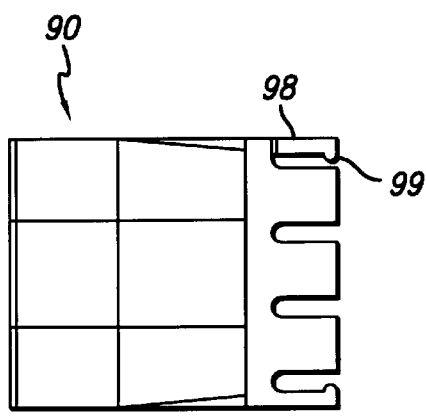
FIG. 8a is a side view and FIG. 8b is a cross-sectional view of a funnel cap in accordance with the present invention.
Figure 8B:
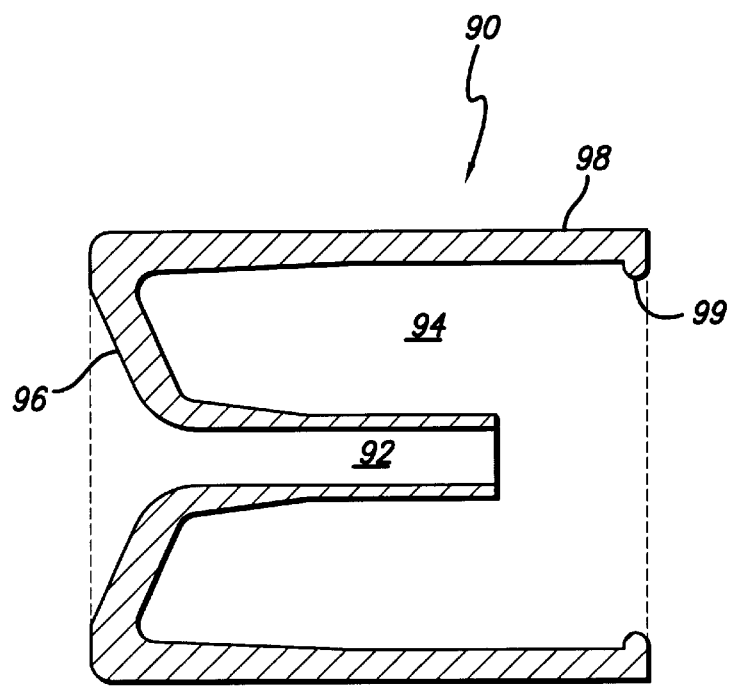

Referring to FIGS. 2, 3, 6a, and 6b, the seal holder 80 contains the entire bleed back control seal 70. The exterior of the seal holder 80 preferably stepped so as to have several diameters which correspond to the staggered interior diameters of the seal cavity 14. For example, the exterior of the seal holder 80 may include a step 83 formed near the distal end of the seal holder 80 which would sit upon or otherwise engage a corresponding ledge formed along the interior surface of the seal cavity 14. The seal holder 80 fits within the contours of the seal cavity 14, and is bonded to the seal cavity 14 by ultrasonic welding or any other suitable technique. The seal holder 80 has an aperture 82 formed in its bottom surface. The seal holder 80 terminates distally with the vertical wall 84. Referring to FIG. 6a, a horizontal flange 86 extends laterally from the vertical wall 84 to form the bottom wall of the interior chamber 88 of the seal holder 80.

The hub 87 is formed at the end of the horizontal flange 86 and protrudes proximally. The flange 86 and hub 87 are formed so that the aperture 82 is formed therethrough. The proximal (or top) surface of the flange 86 supports and conforms substantially to the distal (or bottom) surface of the distal portion 77 of the arms 76 of the bleed back control seal 70. The distal portions 77 may bevel inward. The hub 87 prevents compression of the distal portions 77 of the bleed back control seal 70 into the aperture 82.

The interior chamber 88 of the seal holder 80 is defined by walls 89. The walls 89 may be tapered to have a greater thickness at the top or proximal end of the seal holder 80. The bleed back control seal 70 is supported within interior chamber 88. The diameter of top or proximal interior chamber 88 is slightly smaller than the diameter of the bleed back control seal 70. Accordingly, the walls 89 of the seal holder 80 provide axial and radial support, as well as compression (axial and radial), for the bleed back control seal 70. In one embodiment, the diameter of top or proximal interior chamber 88 is approximately 6% smaller than the diameter of the bleed back control seal 70. The invention is not limited by a precise ratio of the diameters of the interior chamber 88 of the seal holder 80 and the bleed back control seal 70.

In one embodiment, the seal assembly 20 includes a seal retainer 60 having a center hole 126 formed in its surface. The diameter of the center hole 62 of the seal retainer 60 is preferably greater than the maximum, exterior diameter of the dilator 92 of the funnel cap 90. The dilator 92 extends distally through the center hole 62 of the seal retainer 60. The seal retainer 60 preferably includes a flange 64 around the center hole 62. The flange 64 extends from the distal surface of the seal retainer, and encircles the ears 78 of the bleed back control seal 70. The exterior maximum diameter of the seal retainer 60 may be slightly smaller than the outer diameter of the proximal portion of the seal holder 80. The seal retainer 60 is preferably bonded to the seal holder 80 by ultrasound welding or any other suitable technique. The seal retainer 60 restrains the seal holder 80 and the bleed back control seal 70 against movement by the funnel cap 90 of the cap assembly 30. The seal retainer 60 includes a proximal surface which stabilizes and aligns the spring 110. In turn, the spring 110 helps keep the seal retainer 60 in position, especially if no bonding such as ultrasonic welding is utilized.

Referring to FIGS. 2, 3, 5a, 5b, and 5c, the bleed back control seal 70 has distal (or bottom) side arms 76, a web area 72 formed between the arms 76, the distal portions 77 of arms 76, and the upper ears 78. The bleed back control seal 70 is, in one embodiment, substantially in the shape of two concentric cylinders each having a lumen, with a bottom (or distal) chamber 73 divided from a top (or proximal) chamber 75 by the web area 72. The web area 72 is formed at the proximal or top end of the chamber 73 of the larger, bottom (or distal) cylinder formed by the side arms 76. The diameter of the top cylinder formed by the ears 78 is smaller than the diameter of the bottom cylinder formed by the side arms 76. In one embodiment, the chamber 73 formed between the side arms 76 has a diameter larger than the diameter of the chamber 75 formed between the ears 78.

As discussed in relation to FIG. 3, the cap assembly 30 includes the funnel cap 90 having a dilator 92 which is a tube having a lumen extending from the proximal end of the funnel cap 90 to the top chamber 75 of the bleed back control seal 70. The distal end of the dilator 92 is held within the top chamber 75 of the bleed back control seal 70, unless the dilator 92 is moved. As discussed further below, the user can move the dilator 92 distally, and thus cause the bleed back control seal 70 to dilate or open. However, in the unactivated or normal state, the dilator 92 rests close to, but does not impact, the web area 72 of the bleed back control seal 70.

The ears 78 of the bleed back control seal 70 are shaped to conform with the diameter and shape of the dilator 92. In this manner, The ears 78 of the bleed back control seal 70 have an interior diameter smaller than the exterior diameter of the dilator 92. This difference in diameters ensures that the ears 78 provide a seal and inhibit fluids or gases from escaping proximally around the exterior surface of the dilator 92. The proximal end of the ears 78 are formed to surround the dilator 92 when the dilator 92 is in both its disengaged and engaged positions. In this manner, the ears 78 of the bleed back control seal 70 form a seal around the exterior surface of the dilator 92 regardless of how the user manipulates the cap assembly 30.

In one embodiment, the proximal end of the ears 78 may be notched at an angle of approximately 30 degrees to improve seal integrity and aid in alignment of the dilator 92 of the funnel cap 90. The ears 78 surrounding the dilator 92 prevent or inhibit fluid or gas leakage into interior chamber 94 of the funnel cap 90. In some circumstances, it may be undesirable to allow blood or other fluid to enter interior chamber 94 of funnel cap 90, because of a potential increased risk of confusion as to the source of the leakage. Fluid leakage into the interior chamber 94 of the funnel cap 90 may also make it more difficult to engage or depress the funnel cap 90 so as to move the dilator 92. If blood or other fluid were to collect in the interior chamber 94 of the funnel cap 90, trapped fluid may leak or spurt out of the funnel cap 90 when the user depresses or engages the funnel cap 90.

Figure 5A:
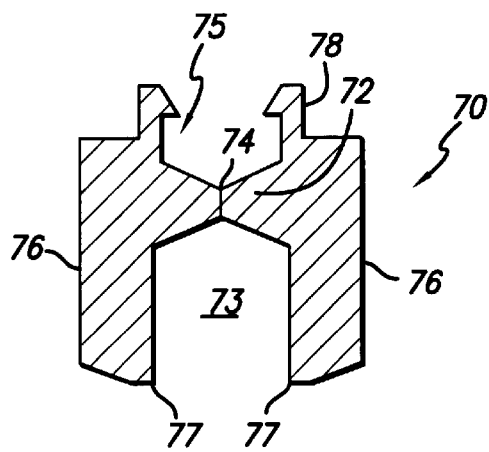
FIG. 5a is a cross-sectional view and FIG. 5b is a perspective view of bleed back control seal in accordance with the present invention.
Figure 5B:
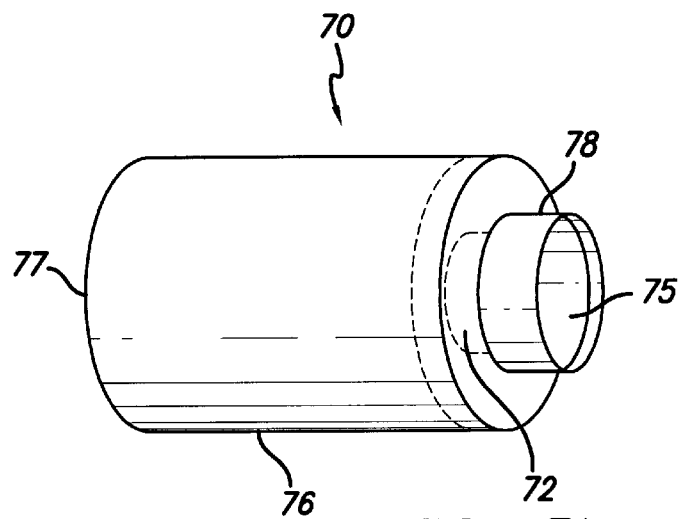

The bleed back control seal 70 has a web area 72 dividing the top chamber 75 from the bottom chamber 73. The web area 72 is roughly perpendicular to the plane of ears 78 and is located distal to ears 78. The web area 72 may be regarded as both the floor of the top chamber 75 and the ceiling of the bottom chamber 73 of the bleed back control seal 70. As shown in FIG. 5b, the web area 72 is substantially disc-shaped.

The web area 72 is thinner at the center and thicker towards the side arms 76. In one embodiment, as shown for example in FIGS. 2, 3, and 5a, the cross-section of the web area 72 is approximately wedge-shaped. In another embodiment, the wedge may be formed at an angle of approximately 115 degrees from the plane of side arms 76. One of ordinary skill would appreciate that the angle of the wedge may differ, and the invention is not limited by the precise angle of the wedge.

The thinning of the web area 72 towards the center provides a balance between sealing and ease of vascular intervention device movement through web area 72. This change in thickness of web area 72 also resists tearing of web area 72 as a vascular intervention device is inserted through web area 72. In one embodiment, web area 72 thins at the middle to a width of approximately 0.023 to 0.031 inches. The invention is not limited by the exact width of web area 72 or the angle of the wedge cross-section of web area 72.

An aperture 74 is formed in the center of the web area 72. In one embodiment, the aperture 74 is formed as a pinhole completely intersecting the web area 72. The aperture 74 is concentric with the lumen 18 of the primary shaft 11 of the side arm body 10. The dilator 92 may be moved distally to stretch the elastomeric material of the web area 72, and cause the aperture 74 to dilate or open wider.

In the normal, disengaged position, in which the dilator 92 does not impact the web area 72, the aperture 74 of the bleed back control seal 70 is closed and inhibits the passage of fluid through the bleed back control seal 70. In the closed or normal position, the web area 72 of the bleed back control seal 70 inhibits fluid communication between the bottom chamber 73 and top chamber 75 of the bleed back control seal 70. In the normally-closed position, the web area 72 of the bleed back control seal 70 inhibits bleed back or loss of fluid from the primary lumen 18 to the dilator 92 of the funnel cap 90.

The invention is not limited by the precise fluid pressures which the bleed back control seal 70 may withstand. The resistance of the bleed back control seal 70 to fluidic pressure may be increased depending on the elastic material used for forming the bleed back control the seal 70 or on the dimensions of the seal 70, including the thickness of the web area 72 and the precise configuration of the aperture 74. In one embodiment, the normally-closed position of the bleed back control seal 70 can withstand fluid pressures of roughly fifteen psi.

Figure 5C:
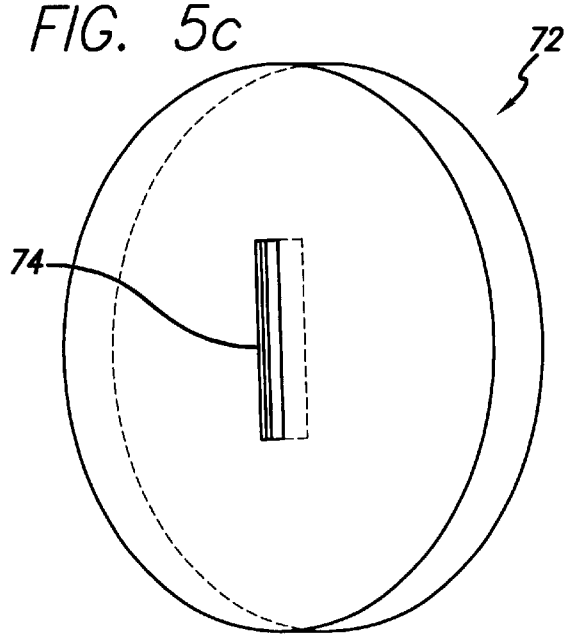
FIG. 5c is a perspective view of a web area of a bleed back control seal in accordance with another embodiment of the present invention.
Figure 5D:
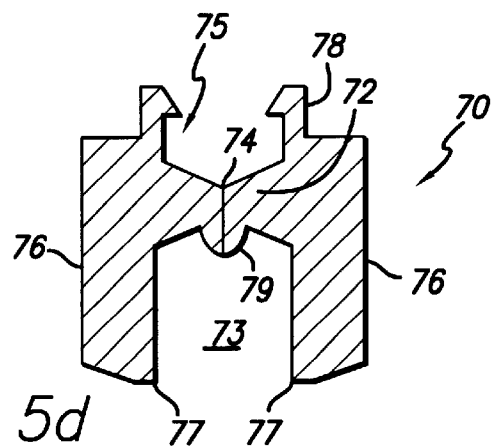
FIG. 5d is a cross-sectional view of a bleed back control seal in accordance with another embodiment of the present invention.

In a preferred embodiment, the web area 72 may have an aperture 74 formed from a single slit 71 as shown in FIG. 5c. In an alternate embodiment, the web area may have an aperture which may be formed with slits and flaps in a tricuspid shape. In another alternate embodiment, the web area 72 may include a spherical portion 79 connected in the center of the distal surface of web area 72, as shown in FIG. 5d. In this embodiment, the aperture 74 extends through the spherical portion 79.

The bleed back control seal 70 extends distally with arms 76 having distal portions 77. In one embodiment, the distal portions 77 may bevel inward, and the invention is not limited by the amount or presence of beveled distal portions 77. As discussed above, the proximal surface of the flange 86 of the seal holder 80 supports the bottom or distal portions 77 of the bleed back control seal 70. The flange 86 terminates in the hub 87. The proximal surface of the flange 86 is shaped to conform substantially to and engage with the distal surface of the distal portions 77 of the arms 76 of the bleed back control seal 70. The hub 87 prevents compression of the distal portions 77 of the bleed back control seal 70 into the aperture 82 of the seal holder 80. The flange 86 and hub 87 of the seal holder 80 also provide rigidity, support, and compression to the bleed back control seal 70. The bleed back control seal 70 is held within the interior chamber 88 formed by the flange 86, hub 87, and walls 89 of the seal holder 80.

Bleed back control seal 70 is made from a suitably elastic polymeric material. In one embodiment, bleed back control seal 70 is made of natural yellowish color polyisoprene having a hardness of 30±5 Shore-A and elongation of approximately 750%. In another embodiment, the bleed back control seal 70 may be formed of a synthetic latex, silicone, or rubber. The bleed back control seal 70 may be sterilized by conventional techniques such as e-beam or ethylene oxide sterilization. Those of ordinary skill will understand that other elastic or resilient materials may be suitable for the bleed back control seal 70. In one embodiment, polyisoprene, manufactured by Lexington Medical, of 30 durometer medical grade may be used.

The elasticity of the material of the bleed back control seal 70 allows the web area 72 to form a seal around a vascular intervention device introduced through the assembly 1. The bleed back control seal 70 is formed of an elastomer with elongation, resilience, and elasticity properties which are sufficient to allow dilation and constriction of the bleed back seal 70, as well as insertion of devices through the aperture 74 of the web area 70, without losing seal integrity. The bleed back control seal 70 is self-sizing and prevents fluid loss or bleed back, while still allowing movement of a vascular intervention device through the bleed back control assembly 1. A user may introduce any appropriate vascular intervention device into the bleed back control assembly 1, such as a catheter (for example, a balloon catheter, an atherectomy catheter, a guidewire, or a stent with delivery system), through the dilator 92, then into the top chamber 75, then through the aperture 74, and then through the bottom chamber 73 of the bleed back control seal 70.

Those of ordinary skill will appreciate that the bleed back control seal 70 can be of varying dimensions. For example, the diameter of the bottom chamber 73 formed by the side arms 76 and the angle of the wedge cross-section of the web area 72 may be changed to improve efficiency. Thus, for example, increasing the diameter of the bottom chamber 73 formed by the side arms 76 may facilitate movement of the dilator 92 of the funnel cap 90 or devices through the aperture 74 of the bleed back control seal 70.

One of ordinary skill will appreciate that any suitable lubricant may be used for bleed back control seal 70. Surface tack may be removed by gas chlorinating at 800±100 parts per million. However, chlorinating may affect device movement or sealing through seal 70. Alternatively, a polydimethyl siloxane liquid lubricant may be used. In one embodiment, Dow 360, 350 centistoke viscosity, may be used as a lubricant. Alternatively, a coating of paralene may be used as a lubricant, or a suitable lubricant may be bonded into the surface of the material of bleed back control seal 70. The invention is not limited by the type (or presence) of lubricant used with bleed back control seal 70.

Cap Assembly

The cap assembly 30 includes the funnel cap 90 and the spring 110. As shown in FIGS. 2 and 3, the funnel 96 of the funnel cap 90, the dilator 92, the center hole 126 of the seal retainer 60, the aperture 74 in the web area 72 of the bleed back control seal 70, the upper chamber 75 and lower chamber 73 of the bleed back control seal 70, the interior chamber 88 and aperture 82 of the seal holder 80, and the aperture 29 and lumen 18 of the side arm body 10 are all substantially aligned along the same axis and are thus all essentially concentric. The seal retainer 60, the seal holder 80, and the funnel cap 90 may be made from any suitable polymeric material, similar to the side arm body 10, and the luer connector 50. In one embodiment, the seal retainer 60, the seal holder 80, and the funnel cap 90 are made of radiation grade polycarbonate.

The funnel cap 90 may have a cylindrical shape, and one embodiment of the funnel cap is octagonal. Referring to FIGS. 2, 3, and 10a to 10c, the funnel cap 90 includes a dilator 92 formed in the interior chamber 94 of the funnel cap 90. The dilator 92 has a lumen extending distally away from funnel surface 96 of funnel cap 90. The dilator 92 is concentric with the lumen 18 of the side arm body 10. The dilator 92 is thus a tube with a lumen connecting (at the proximal end) the exterior of bleed back control assembly 1 with the interior of top chamber 75 of bleed back control seal 70 (at the distal end). The funnel cap 90 is proximal to the bleed back control seal 70 and, in the disengaged position, the distal end of dilator 92 is proximal to and slightly separated from the web area 72 of the bleed back control seal 70. The lumen of the dilator 92, in one embodiment, does not taper or change diameter, but those of ordinary skill will appreciate that the lumen of the dilator 92 may taper or widen without departing from the scope of the invention.

The funnel cap 90 has a proximal exterior surface which tapers in the center to form the shape of a funnel 96 leading into the lumen of the dilator 92. The funnel 96 of the funnel cap 90 is concentric with the lumen of the dilator 92. The maximum diameter of the funnel 96, in one embodiment, may be approximately 73% of the diameter of the proximal surface of funnel cap 90. The invention is not limited by the precise ratio of the diameters of the funnel 96 and proximal surface of the funnel cap 90. The funnel 96 improves the loading or self-locating of guidewires, catheters, and other devices as the operator seeks to introduce them into the bleed back control assembly 1. In one embodiment, the funnel 96 may be formed at approximately a 25 degree angle from the plane of proximal surface of the funnel cap 90. The invention is not limited by the angle at which the funnel 96 is formed, nor by the diameter of the funnel 96 as compared to the diameter of the funnel cap 90.

Surrounding the dilator 92 and disposed within the interior chamber 94 of the funnel cap 90 is the return spring 110. The ends of the spring 110 may be squared. In one embodiment, the spring 110 may have a spring rate of approximately 3.9 lbs./inch.

The proximal end of the spring 110 abuts the interior surface of the proximal end of the funnel cap 90. As discussed below, the distal end of the spring 110 abuts and sits atop the seal retainer 60. In this embodiment, the placement of the distal end of the spring 110 on the seal retainer 60 helps stabilize and align the spring 110, while the spring 110 helps keep the seal retainer 60 in place. In an alternate embodiment, the proximal surface of the seal holder 80 may be formed to abut and support the distal end of the spring 110.

The windings or coils of the spring 110 surround the exterior surface of the dilator 92. In one embodiment, the spring 110 may have approximately five windings or coils. The invention is not limited by the diameter or spacing or number of the windings of spring 110. The spring 110 acts to return the funnel cap 90 to the original or normal position when released, so that the dilator 92 will not dilate the aperture 74 of the bleed back control seal 70 when the user releases the funnel cap 90.

The spring 110 may be of any suitable material, and in one embodiment may be formed of 302 stainless steel wire. In one embodiment, the spring 110 has ends which may be squared. The invention is not limited by the material out of which the spring 110 is formed.

The exterior surface of the funnel cap 90 exterior surface extends distally and terminates in arms 98. In an embodiment in which the funnel cap 90 is octagonal, the funnel cap 90 has eight arms 98. An overhanging lip 99 is formed at the distal edge or bottom of arms 98, and the overhanging lip 99 extends generally inward towards the interior chamber 94 of the funnel cap 90. The overhanging lip 99 of the funnel cap 90 grips the outer surface at the bottom edge of the proximal end 12 of the side arm body 10. Additionally, the arrangement of overhang 99 with a jutting outer edge 21 of the proximal end 12 of the side arm body 10 allows funnel cap 90 to be moved distally, thus allowing the dilator 92 to move distally as well through the bleed back control seal 70. Where the funnel cap 90 has an octagonal shape, the exterior of the proximal end 12 of the side arm body would have a corresponding octagonal shape to allow axial movement of the funnel cap. Additionally, the arrangement of funnel cap 90 with the proximal end of the side arm body 10 allows the spring 110 to be held in a compressible manner, so as to allow the spring 110 to return the funnel cap 90 to its original or normal position after being released. The invention is not limited by the number of the arms 98 or the shape of the overhang 99.

As discussed above, the user may operate the cap assembly 30 to open or close the seal assembly 20. The operation and interaction between cap assembly 30 and seal assembly 20 will be discussed next.

Operation of Bleed Back Control Seal

The bleed back control seal 70 of the seal assembly 20 is normally closed unless acted upon. The user of the bleed back control assembly 1 may open the bleed back control seal 70 by dilating the aperture or pinhole 74. Because the bleed back control seal 70 has an aperture 74 in the center of the web area 72, and because the material of the bleed back control seal 70 is highly elastic and resilient, stretching of the web area 72 will cause the aperture 74 to open larger, thus allowing the bleed back control seal 70 to open. The web area 72 is elastic and relisient, and will return to the original, closed position when released after being stretched, thus closing the aperture 74.

The user may push or press the funnel cap 90 and thus move the dilator 92 distally to open or dilate the bleed back control seal 70. A user of bleed back control assembly 1 may depress the funnel cap 90 axially towards the distal end 16 of the side arm body 10. This pressing or engaging of the funnel cap 90 will also cause the dilator 92 to move axially and distally. When the funnel cap 90 is pushed, the dilator 92 will abut the web area 72 of the bleed back control seal 70.

Axial movement of the funnel cap 90 and dilator 92 causes the bleed back control seal 70 to open by stretching the material of web area 72 distally. The web area 72 will be stretched and pushed into the chamber 73 of the bleed back control seal 70. This stretching of the web area 72 will cause the aperture 74 to open wider or dilate. Pushing the funnel cap 90 also causes the spring 110 to constrict or compress. The dilator 92 may be moved distally until the dilator 92 is blocked by impact with the hub 87 and flange 86 of the seal holder 80.

The diameter of bottom chamber 73 formed by the side arms 76 of the bleed back control seal 70 is larger than the diameter of the dilator 92. This difference in diameters provides a break away for the material of web area 72 as web area 72 is pushed and stretched into bottom chamber 73 as the dilator 92 moves distally.

The return spring 110, wound around the exterior of the dilator 92 and inside chamber 94 of the funnel cap 90, causes the funnel cap 90 to return to the starting, original position when the user releases or stops pushing the funnel cap 90. The decompressing action of the spring 110 moves the dilator 92 proximally, thus allowing the bleed back control seal 70 to return to its original shape and close the aperture 74 again. Removal of the dilator 92 away from the web area 72 of the bleed back control seal 70 causes the bleed back control seal 70 to close by allowing the resilient material of web area 72 to return to its original shape and position. As the elastic material of web area 72 contracts back to its original shape, the aperture 74 will correspondingly grow smaller, until eventually the aperture 74 formed in the web area 72 of the bleed back control seal 70 will close.

During use of the bleed back control assembly 1, a user may decide to introduce a device (such as a catheter or guidewire) into the bleed back control assembly 1. The user may insert a device into the funnel surface 96 of the funnel cap 90. The device then continues into the lumen of the dilator 92, and through the aperture 74 of the bleed back control seal 70. The user may choose to dilate the aperture 74 depending on the size of inserted device. The device then continues through aperture 82 in the bottom of the seal holder 80, and enters the lumen 18 of the side arm body 10. Continued insertion will cause the device to move through the lumen 18, through the lumen 52 in the luer connector 50, and ultimately into the patient's body in any suitable or desired location and structure, either transluminally, transvenously, or in any other appropriate diagnostic or interventional manner.

A user may dilate the aperture 74 of the bleed back control seal 70 before inserting a device through the aperture 74. A user may engage the funnel cap 90 and the dilator 92, push them axially and distally, and thereby open or dilate the aperture 74 of the bleed back control seal 70 to allow greater ease of insertion of device. Dilation of the bleed back control seal 70 may not be necessary for insertion of many devices such as catheters and guidewires.

An operator of the bleed back control assembly 1 may introduce a guidewire, catheter, or other desired device through the funnel cap 90 into the dilator 92, through the dilated aperture 74 of the bleed back control seal 70, through the bottom chamber 73 of the bleed back control seal 70, through the aperture 82 of the seal holder 80, then into the primary lumen 18 of the side arm body 10, and ultimately into the patient.

A device may be removed by withdrawing the device back through these same structures in reverse order. Both during insertion and withdrawal, the user may choose to dilate or stop dilating the aperture 74 of the bleed back control seal 70, at any time.

One of ordinary skill would understand that the device may be any appropriate transluminal or interventional device. For example, the device may be a catheter, stent, guidewire, balloon catheter, or any other suitable device. A user desiring to introduce a stent into bleed back control assembly 1 may introduce the stent without necessarily requiring use of the dilator 92 to open the aperture 74 of the bleed back control seal 70. Guidewires may be introduced into bleed back control assembly 1 with an introducer and, if an introducer is used, then the aperture 74 of the bleed back control seal 70 does not need to be opened with the dilator 92. A balloon catheter may also be introduced into the bleed back control assembly 1 without necessarily dilating the bleed back control seal 70.

The elastic and resilient material properties of the bleed back control seal 70 allow the web area 72 to be self-sizing around device introduced through the aperture 74 of the bleed back control seal 70. The bleed back control seal 70 inhibits the loss of blood or other fluids when a device is inserted through the aperture 74 of the bleed back control seal 70. The bleed back control seal 70 thus controls fluid or blood loss both with and without devices intratubal. A device penetrating the bleed back control seal 70 can be moved into and out of the side arm body 10 with substantially low fluid leakage and resistance.

A user may manipulate the funnel cap 90 and dilator 92 to open the bleed back control seal 70 and allow the purging of gases or undesired fluids from the interior of the bleed back control assembly 1. A user may push or press the funnel cap 90 and dilator 92 to cause the aperture 74 to open and allow the pressure of fluids within the bleed back control assembly 1 to purge gases or fluids trapped inside the assembly 1. The gases or fluids exit dilator 92 and out through the proximal end of the assembly 1.

The bleed back control assembly controls blood loss during insertion, movement, and removal of devices from the assembly. While several aspects of the invention have been described with regard to specific embodiments, those skilled in the art will recognize that changes can be made in form and detail without departing from the spirit and scope of the invention. The various components and sub-assemblies described with respect to the disclosed embodiments may be rearranged or combined with each other without departing from the scope of the invention. Changes can be made to dimensions, sizing, relative dimensions, materials, spatial and angular relationships of and between components, and manufacturing processes and other commercial or industrial techniques, without departing from the scope of the invention.

What is claimed is:

1. A bleed back control assembly comprising:
   a body having a proximal end, a distal end, and a lumen connecting the proximal and distal ends;
   a seal cavity formed in the proximal end of the body, wherein the seal cavity has an interior distal surface including an aperture allowing fluid communication between the lumen of the body and the seal cavity;
   a single elastomeric seal contained within the seal cavity, the elastomeric seal having an aperture, which is closed unless acted upon, wherein the elastomeric seal includes a top cylindrical section having a lumen, a bottom cylindrical section with a lumen having a larger diameter tan the top cylindrical section lumen, and a web area dividing the lumen of the top cylindrical section from the lumen of the bottom cylindrical section;
   a seal holder having an interior chamber, wherein the seal holder is bonded to the seal cavity, and the elastomeric seal is located within the interior chamber of the seal holder; and
   a cap assembly coupled to the proximal end of the body.

2. The bleed back control assembly of claim 1, further comprising a seal retainer adjacent to the seal holder, wherein the seal retainer restrains the elastomeric seal against movement by the cap assembly.

3. The bleed back control assembly of claim 1, wherein the elastomeric seal is located entirely within the interior chamber of the seal holder.

4. The bleed back control assembly of claim 1, further comprising:
   a secondary branch having a secondary lumen allowing fluid communication with the lumen of the body, and
   a finger rest formed on the exterior surface of the secondary branch.

5. The bleed back control assembly of claim 1, wherein the cap assembly further includes a dilator for opening the aperture of the elastomeric seal, and the elastomeric seal further includes ears for forming a seal around the dialator.

6. The bleed back control assembly of claim 1, wherein the cap assembly includes a funnel lumen having an inner diameter no less than about 0.118 inches.

7. The bleed back control assembly of claim 1, wherein the lumen of the body has an inner diameter of about 0.118 inches.

8. The bleed back control assembly of claim 1, further comprising a spring for biasing the cap assembly away from the elastomeric seal.

9. A bleed back control assembly comprising:

a body having a proximal end, a distal end, and a lumen connecting the proximal and distal ends;

a seal cavity formed in the proximal end of the body, the lumen being in fluid communication with the seal cavity;

a cap assembly coupled to the proximal end of the body, wherein the cap assembly encloses the seal cavity;

a seal holder having an interior chamber, wherein the seal holder is bonded to the seal cavity;

a seal retainer adjacent to the seal holder, wherein the seal retainer restrains the elastomeric seal against movement by the cap assembly;

a single elastomeric seal contained within the seal cavity, the elastomeric seal having a normally-closed aperture, wherein the elastomeric seal is located entirely within the interior chamber of the seal holder and wherein the elastomeric seal includes a top cylindrical section having a lumen, a bottom cylindrical section with a lumen having a larger diameter than the top cylindrical section lumen, and a web area dividing the lumen of the top cylindrical section from the lumen of the bottom cylindrical section;

wherein the cap assembly is operable to open the normally-closed aperture of the elastomeric seal.

10. The bleed back control assembly of claim 9, wherein the elastomeric seal is located entirely within the interior chamber of the seal holder.

11. The bleed back control assembly of claim 9, further comprising:

a secondary branch having a secondary lumen allowing fluid communication with the lumen of the body, and a finger rest formed on the exterior surface of the secondary branch.

12. The bleed back control assembly of claim 9, wherein the cap assembly further includes a dilator for opening the aperture of the elastomeric seal, and the elastomeric seal further includes ears for forming a seal around the dialator.

13. The bleed back control assembly of claim 9, wherein the cap assembly includes a funnel lumen having an inner diameter no less than about 0.118 inches.

14. The bleed back control assembly of claim 9, wherein the lumen of the body has an inner diameter of about 0.118 inches.

15. The bleed back control assembly of claim 9, further comprising a spring for biasing the cap assembly away from the elastomeric seal.

16. A bleed back control assembly comprising:

a body having a proximal end, a distal end, and a lumen connecting the proximal and distal end;

a seal cavity formed in the proximal end of the body, the lumen being in fluid communication with the seal cavity;

a seal holder having an interior chamber, wherein the seal holder is bonded to the seal cavity;

a seal cavity formed in the proximal end of the body, wherein the lumen is in fluid communication with the seal cavity;

the seal cavity having a single elastomeric means for sealing, wherein the elastomeric means for sealing has a normally-closed aperture, and wherein the elastomeric means for bleed back sealing includes a top cylindrical section having a lumen, a bottom cylindrical section with a lumen having a larger diameter than the top cylindrical section lumen, and a web area dividing the lumen of the top cylindrical section from the lumen of the bottom cylindrical section; and a cap assembly coupled to the proximal end of the body, wherein the cap assembly is operable to open the normally-closed aperture of the elastomeric means for sealing.

17. The bleed back control assembly of claim 16 further comprising a seal retainer adjacent to the seal holder, wherein the seal retainer restrains the elastomeric means for sealing against movement by the cap assembly.

18. The bleed back control assembly of claim 16, wherein the elastomeric means for sealing is located entirely within the interior chamber of the seal holder.

19. The bleed back control assembly of claim 16, further comprising:

a secondary branch having a secondary lumen allowing fluid communication with the lumen of the body, and a finger rest formed on the exterior surface of the secondary branch.

20. The bleed back control assembly of claim 16, wherein cap assembly includes a dilator for opening for the normally-closed aperture of the elastomeric means for sealing, and the elastomeric means for sealing includes ears for forming a seal around the dilator.

21. The bleed back control seal of claim 16, wherein the cap assembly includes a funnel lumen having an inner diameter no less than about 0.118 inches.

22. The bleed back control seal of claim 16, wherein the lumen of the body has an inner diameter of about 0.118 inches.

23. The bleed back control assembly of claim 16, further comprising a spring for biasing the cap assembly away from the elastomeric means for sealing.

24. A bleed back control assembly comprising:

a body having a proximal end, a distal end, and a lumen connecting the proximal and distal ends;

a seal cavity formed in the proximal end of the body, wherein the seal cavity has an interior distal surface including an aperture allowing fluid communication between the lumen of the body and the seal cavity;

a seal holder having an interior chamber;

a single bleed back control seal having a normally-closed aperture, wherein the bleed back control seal is positioned within the interior chamber of the seal holder, and the seal holder is positioned within the seal cavity;

a cap assembly coupled to the proximal end of the body; and a spring for biasing the cap assembly away from the bleed back control seal.

25. The bleed back control assembly of claim 24, wherein the seal holder is bonded to the seal cavity.

26. The bleed back control assembly of claim 24, wherein the bleed back control seal comprises:

a top cylindrical section having a lumen;

a bottom cylindrical section with a lumen having a larger diameter than the top cylindrical section lumen; and a web area dividing the lumen of the top cylindrical section from the lumen of the bottom cylindrical section.

27. The bleed back control assembly of 24, wherein the cap assembly retains the bleed back control seal within the seal cavity.

* * * * *

UNITED STATES PATENT AND TRADEMARK OFFICE
CERTIFICATE OF CORRECTION

PATENT NO. : 6,695,820 B1
DATED : February 24, 2004
INVENTOR(S) : Armstrong et al.

It is certified that error appears in the above-identified patent and that said Letters Patent is hereby corrected as shown below:

Column 12,
Line 40, delete "tan" and insert -- than --.

Column 13,
Line 55, delete "end;" and insert -- ends; --.

Signed and Sealed this

Seventeenth Day of August, 2004

JON W. DUDAS
*Acting Director of the United States Patent and Trademark Office*